United States Patent

Bremer et al.

[11] Patent Number: 6,054,683
[45] Date of Patent: Apr. 25, 2000

[54] CARTRIDGE HEATER FOR A GAS CHROMATOGRAPHY TRANSFER DEVICE

[75] Inventors: Ralf Bremer, Oberhausen; Bernhard Rose, Dusseldorf, both of Germany

[73] Assignee: Gerstel GmbH & Co., KG, Mulheim, Germany

[21] Appl. No.: 09/293,674

[22] Filed: Apr. 16, 1999

[30] Foreign Application Priority Data

Apr. 17, 1998 [DE] Germany ............................ 198 17 017

[51] Int. Cl.[7] .......................... B01D 15/08; G01N 31/00; H05B 1/02
[52] U.S. Cl. .......................... 219/388; 219/407; 219/534; 219/553; 392/480; 96/101; 73/863.11; 73/864.81
[58] Field of Search .................................. 219/388, 385, 219/534–536, 543, 544, 546, 548, 552, 553, 407; 392/480, 482; 73/23.42, 863.11, 864.81; 422/78, 89; 356/312; 96/101–107

[56] References Cited

U.S. PATENT DOCUMENTS

| | | | |
|---|---|---|---|
| 1,718,106 | 6/1929 | Bolsinger | 392/480 |
| 2,522,365 | 9/1950 | Greene | 392/480 |
| 2,721,729 | 10/1955 | van Riper | 392/480 |
| 2,836,248 | 5/1958 | Covington | 392/480 |
| 4,766,760 | 8/1988 | Poshemansky et al. | 73/23.35 |
| 5,236,668 | 8/1993 | Higdon | 422/89 |
| 5,544,276 | 8/1996 | Loux et al. | 392/480 |
| 5,702,671 | 12/1997 | Gerstel | 73/863.11 |
| 5,827,353 | 10/1998 | O'Neil | 96/101 |
| 5,944,877 | 8/1999 | O'Neil | 96/101 |

*Primary Examiner*—Joseph Pelham
*Attorney, Agent, or Firm*—Townsend and Townsend and Crew LLP

[57] ABSTRACT

The invention relates to a cartridge heater for a gas chromatography transfer device for substances which are to be analyzed, having a metal tube for accommodating a tube section to be heated and a heating coil arranged outside the metal tube, the metal tube bearing, on the outside, a groove which corresponds to the shape of the heating coil and in which a heating conductor is embedded in an electrically insulated manner with respect to the metal tube.

10 Claims, 2 Drawing Sheets

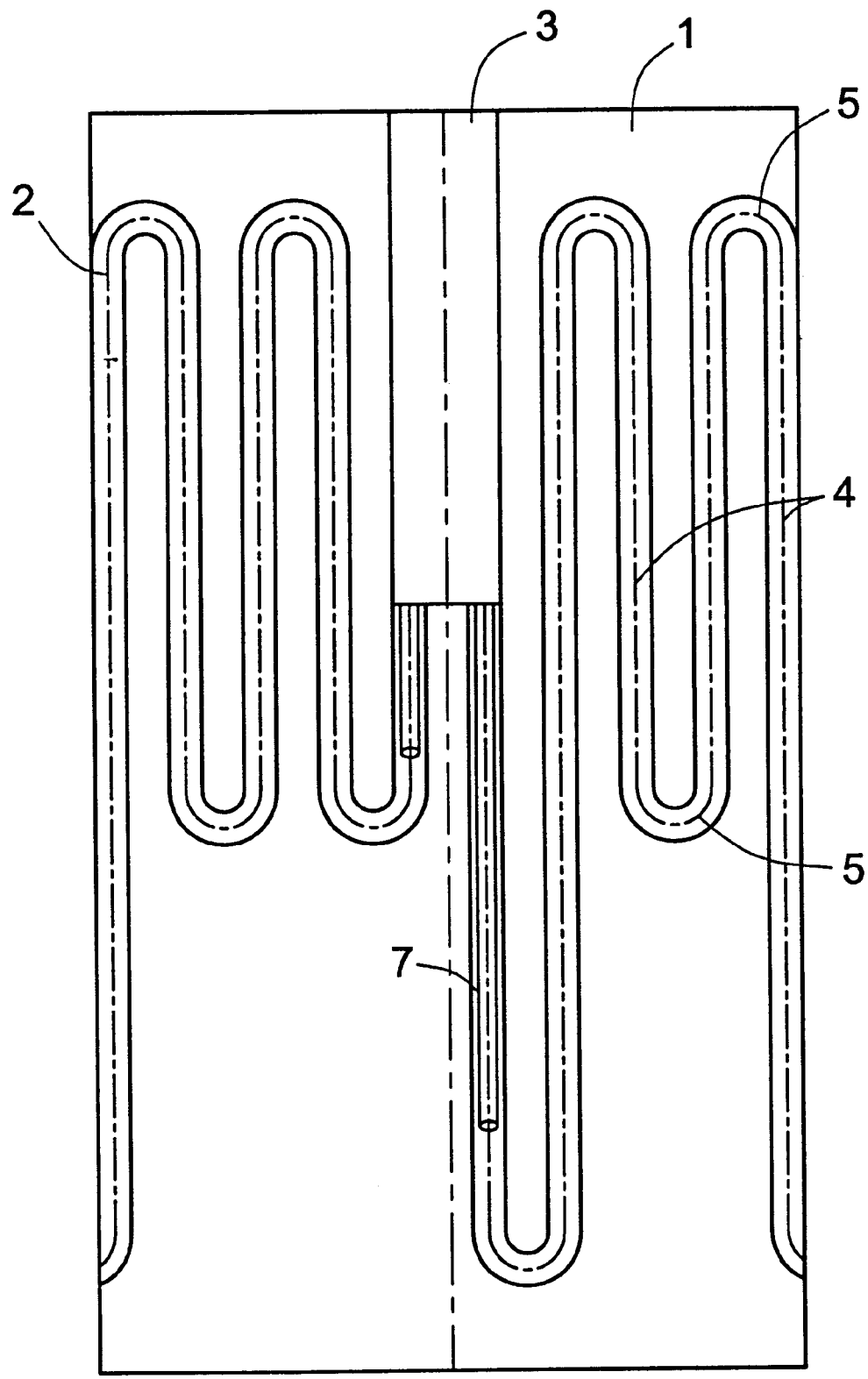

CARTRIDGE HEATER FOR A GAS CHROMATOGRAPHY TRANSFER DEVICE

FIELD OF THE INVENTION

The invention relates to a cartridge heater for a gas chromatography transfer device for samples which are to be analyzed, for example for transfer from an application device to a gas chromatography capillary column or the like.

DESCRIPTION OF THE RELATED ART

German Patent DE 195 20 715 C1 discloses a gas chromatography transfer line which has a glass tube, a steel tube surrounding the glass tube and a heating coil, a tube which is made from material with a good thermal conductivity and is for its part provided with openings and soldered to the heating coil and the steel tube, is arranged between the glass tube and the steel tube. In this case, the solder fills even the openings and the space between the tube made from material with a good thermal conductivity and the steel tube. However, the fact that this line is complex and expensive to produce, while the turns of the heating coil are relatively inaccurate, particularly if different winding densities are required, and the complex and expensive soldering of the coil represent drawbacks of this line.

SUMMARY OF THE INVENTION

One object of the invention is to provide a cartridge heater for a gas chromatography transfer device which allows more simple production with reduced tolerances.

A subject of the invention is a cartridge heater for a gas chromatography transfer device for substances to be analyzed, comprising:

a metal tube for accommodating a tube section to be heated; and a heating coil arranged outside the metal tube;

wherein the metal tube bears, on the outside, a groove which corresponds to the shape of the heating coil and in which a heating conductor is embedded in an electrically insulated manner with respect to the metal tube.

Further objects, advantages and embodiments of the invention are evident from the following description.

The invention is explained in more detail hereinafter by means of exemplary embodiments of the invention shown in the attached drawings.

BRIEF DESCRIPTION OF THE DRAWINGS

FIG. 3 shows a developed view of a further embodiment of a cartridge heater.

DESCRIPTION OF PREFERRED EMBODIMENTS

Figure 1:
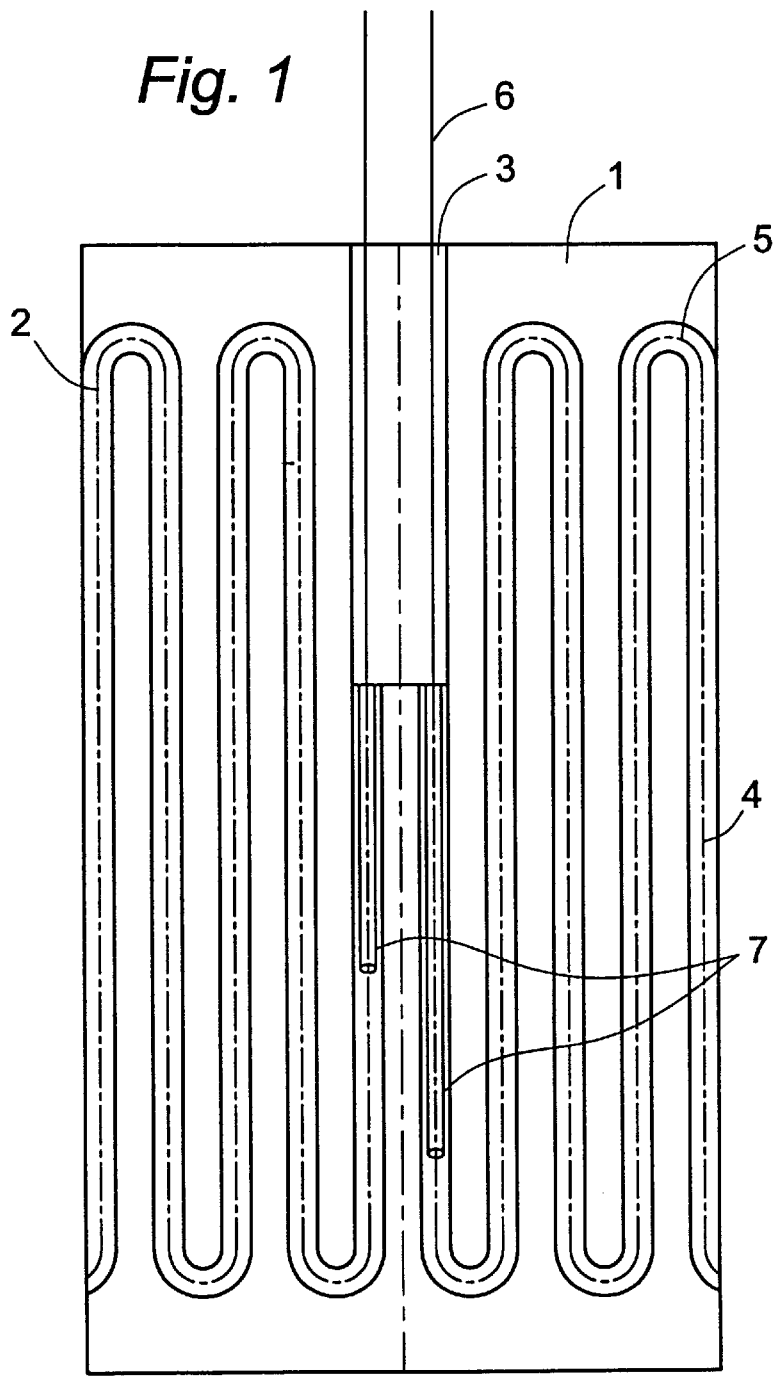
FIG. 1 shows a developed view of a cartridge heater for a gas chromatography transfer device according to the invention.
Figure 2:
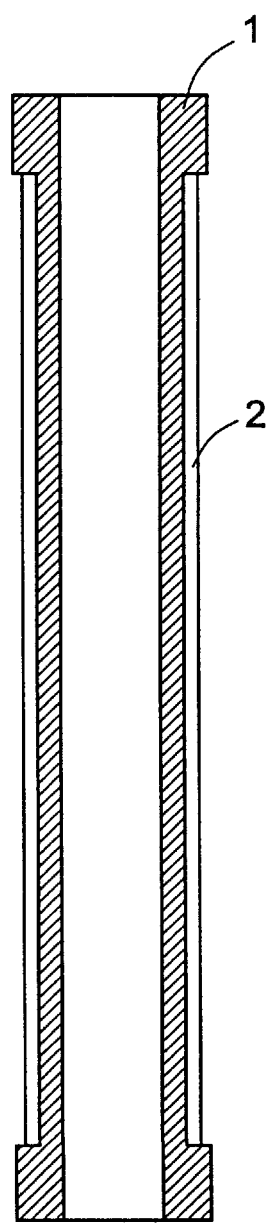
FIG. 2 shows a sectional view of a metal tube for the cartridge heater of FIG. 1.

The cartridge heater, which is illustrated in FIG. 1 and 2, for a gas chromatography transfer device for substances to be analyzed comprises a metal tube 1 which is used to accommodate a tube section which is to be heated of a sample injector (cold application device, thermodesorption device or the like), a cryotrap, a transfer line or the like, for example a sample application tube, as can be found, for example, in German Patent DE 195 20 715 C1. The tube section which is to be heated can be heated up in a temperature-controlled manner in appropriate working cycles of a gas chromatograph, for which purpose low voltage of<42 V, generally 24 V, which is present in the system, is used. As a result, substances which are to be analyzed and, if appropriate, to be masked out are evaporated in the area of the tube section which is to be heated, so that they can be removed by means of carrier gas.

The metal tube 1 has a groove 2 which is milled or molded into its outer side. The groove 2 is in this case designed in meandering form, starts from a relatively wide groove section 3 and then opens back out into this section, forming a multiplicity of loops which comprise straight sections 4, which extend in the longitudinal direction of the metal tube 1, and joining sections 5, which join these straight sections, near to the ends of the metal tube 1.

The widened groove section 3, which opens out at one end of the metal tube 1, accommodates a section of a connection line 6, while the groove 2 accommodates a heating conductor 7 (only part of which is shown) in an electrically insulated manner with respect to the metal tube 1, which conductor forms a corresponding heating coil.

The groove 2 may also open out directly at one or both ends of the metal tube 1, the first of these options being preferred, since in that case the feed lines are situated at only one end of the metal tube 1.

The groove 2 may also be in the form of a double groove, in order to provide a bifilar winding of the heating conductor 7. The groove 2 may also be arranged in a spiral instead of meandering form. Furthermore, the groove 2 may be arranged in such a way that different heating winding densities and therefore different heating capacities are produced on different sections, as seen over the length of the metal tube 1, so that it is possible to achieve an appropriate temperature distribution over the length of the metal tube 1, see the embodiment illustrated in FIG. 3.

The metal tube 1 may be provided with an electrically insulating coating on the outer side. This may be a layer of insulating varnish or a layer of insulating metal oxide. In the case of a metal tube 1 which is made from aluminum, this aluminum may be oxidized on the outer side, so as to form the layer of oxide. However, metal oxide may also be applied by flame spraying.

If the metal tube 1 has an electrically insulating coating on the outside or in the groove 2, the heating conductor 7 may be installed without insulation. Otherwise, the heating conductor 7 is to be insulated, for example by using a heating wire which is surrounded by glass filaments.

If the heating conductor 7 is used without insulation, it may be laid into the groove 2 as a heating wire and cemented into this groove by means of water glass or the like. However, it may also be introduced into the groove 2 in the form of a conductive, hardenable paste.

Furthermore, the metal tube 1 may be provided, at any desired location, with a thermocouple as a temperature sensor for controlling the heating of a tube section which is to be heated of a sample injector, a cryotrap, a transfer line or the like which is bought about by the cartridge heater.

Moreover, the cartridge heater may have an outer sleeve (not shown), in particular made from metal, which serves as a protective casing for the cartridge heater.

A structure of this nature can readily be produced with sufficient accuracy with regard to the winding density of the heating conductor 7 for different lengths of this conductor, so that a desired temperature profile can be set along the cartridge heater. There is no need to solder on the heating conductor 7. Also, it is possible to produce higher temperatures, which exceed the melting temperature of the solder, than with a heating conductor which has been soldered on.

Although the foregoing has been a description of preferred embodiments of the invention, it will be apparent to those skilled in the art that numerous variations and modifications may be made to the invention without departing from the scope as described herein.

What is claimed is:

1. A cartridge heater for a gas chromatography transfer device for substances which are to be analyzed, comprising:
    a metal tube for accommodating a tube section to be heated; and
    a heating coil arranged outside the metal tube;
    wherein the metal tube bears, on the outside, a groove which corresponds to the shape of the heating coil and in which a heating conductor is embedded in an electrically insulated manner with respect to the metal tube.

2. The cartridge heater of claim 1, in which the metal tube is provided with an electrically insulating coating on the outside.

3. The cartridge heater of claim 2, in which the electrically insulating coating is a layer of oxide.

4. The cartridge heater of claim 1, in which the heating conductor is a heating wire which bears an electrically insulating sheathing.

5. The cartridge heater of claim 1, in which the heating conductor is cemented into the groove.

6. The cartridge heater of claim 1, in which the groove is in serpentine form.

7. The cartridge heater of claim 1, in which the free ends of the heating conductor are situated at one end of the cartridge heater.

8. The cartridge heater of claim 1, in which the winding density of the heating conductor over the length of the metal tube is adapted to the heating capacity required.

9. The cartridge heater of claim 1, in which a thermocouple is arranged on the metal tube, as a temperature sensor.

10. The cartridge heater of claim 1, in which an outer sleeve is provided as a casing.

* * * * *